United States Patent [19]

Brois

[11] 4,042,523
[45] Aug. 16, 1977

[54] OLEFIN-THIONOPHOSPHINE SULFIDE REACTION PRODUCTS, THEIR DERIVATIVES AND USE THEREOF AS OIL AND FUEL ADDITIVES

[75] Inventor: Stanley J. Brois, Westfield, N.J.

[73] Assignee: Exxon Research and Engineering Co., Linden, N.J.

[21] Appl. No.: 622,161

[22] Filed: Oct. 14, 1975

Related U.S. Application Data

[63] Continuation of Ser. No. 452,955, March 20, 1974, abandoned.

[51] Int. Cl.² .................................................. C10M 1/48
[52] U.S. Cl. ............................. 252/32.7 HC; 252/37; 252/46.6; 252/46.7; 44/68; 44/72
[58] Field of Search ............. 252/32.7 HC, 46.6, 46.7, 252/37; 44/68, 72, 76

[56] References Cited

U.S. PATENT DOCUMENTS

| | | | |
|---|---|---|---|
| 2,640,053 | 5/1953 | Hill et al. | 252/32.7 HC X |
| 2,712,528 | 7/1955 | Hill et al. | 252/32.7 HC X |
| 2,865,907 | 12/1958 | Verley | 252/46.6 X |
| 3,329,612 | 7/1967 | Ferm et al. | 252/32.7 HC X |
| 3,520,808 | 7/1970 | Light | 252/46.6 |
| 3,560,384 | 2/1971 | Halling | 252/32.7 HC X |
| 3,826,797 | 7/1974 | Brois | 260/125 |
| 3,865,810 | 2/1975 | Haugen et al. | 252/32.7 HC |
| 3,966,622 | 6/1976 | Hellmuth et al. | 252/46.6 |

Primary Examiner—Delbert E. Gantz
Assistant Examiner—Andrew H. Metz
Attorney, Agent, or Firm—Frank T. Johmann

[57] ABSTRACT

Adducts are formed in a process which involves the reaction of an olefin, including olefin polymers, with a dimeric thionophosphine sulfide. Further derivatives may be formed by reacting the resulting olefin-thionophosphine sulfide adduct products with amines, e.g., alkylene polyamines, aziridines, phosphines or metal salts, e.g., zinc salts. Or, alkylene polyamine- or aziridine- treated olefin-thionophosphine sulfide reaction products may be further reacted with metal salts, e.g., zinc acetate. A representative material can be prepared by reacting polyisobutylene with an arylthionophosphine sulfide, and then further reacting the resulting cyclic bis(phosphinodithioic acid) anhydride product with an alkylene polyamine or aziridine, which in turn, may be further modified by reaction with zinc acetate.

The oil soluble olefin-thionophosphine sulfide products, as well as its oil soluble derivatives outlined above, may be used as additives for lubricating oil, and petroleum fuels, e.g., gasoline or fuel oil.

10 Claims, No Drawings

# OLEFIN-THIONOPHOSPHINE SULFIDE REACTION PRODUCTS, THEIR DERIVATIVES AND USE THEREOF AS OIL AND FUEL ADDITIVES

This is a continuation of application Ser. No. 452,955, filed Mar. 20, 1974, and now abandoned.

BACKGROUND OF THE INVENTION

This invention relates to a process for making adducts via the reaction of olefins, including polyolefins, with dimeric thionophosphine sulfides, the products of said process, various derivatives thereof, and use of said products and derivatives as lubricating oil and fuel additives.

It has been known that phosphosulfurized hydrocarbons, such as olefins, particularly polyisobutylene, reacted with phosphorus pentasulfide ($P_2S_5$) can exhibit detergent effects in lube oil and fuel, as well as oxidation inhibition properties. However, while various phosphosulfurized hydrocarbons have been known in the art (J. R. van Wazer, *Phosphorus and Its Compounds*. Interscience Publishers, Inc., New York, 1961, Vol. II, p. 1276–1277), in general they are acidic and usually are complex and undefined products which vary in composition depending on reaction conditions and reagent ratio. Also, they frequently undergo hydrolytic degradation to give corrosive, inorganic phosphoric and thiophosphoric acids (e.g., see U.S. Pat. No. 3,185,728). Neutralization of these acidic $P_2S_5$ hydrocarbons, with metallic and amine bases, frequently engenders low molecular weight metal and amine thiophosphate salts, which salts in turn, are potential sources of sludge and sediment, tending to adversely affect any detergent properties otherwise present. Contrary to many of the prior phosphosulfurized hydrocarbons, the process of the present invention can give stable, structurally well-defined phosphorus and sulfur containing compositions useful as additives, and which do not ordinarily yield inorganic phosphoric acids upon hydrolysis. Also, these inventive materials when reacted, e.g., with an amine, can exhibit potent dispersant-inhibitor properties.

SUMMARY OF THE INVENTION

The present invention includes compositions, and their use in lubricating oil and fuel, which compositions are the reaction product (adduct) of (1) an olefin, including polyolefins, and (2) a dimeric thionophosphine sulfide having the structure:

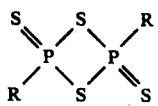

wherein R is an organic radical of 1 to 18 carbon atoms, and generally will be selected from the group consisting of alkyl, cycloalkyl and aryl radicals. The invention also contemplates derivatives of the above-noted olefin-thionophosphine sulfide adducts, formed by reacting the olefin-thionophosphine sulfide adducts with amines, e.g., alkylene polyamines, aziridines, phosphines, or metal salts. The invention also includes processes for making said adducts and derivatives.

In general, the basic thionophosphine sulfide-olefin adduct has been found to be an oxidation inhibitor and when made from a high molecular weight olefin, has some detergency. The polyamine and ethylenimine-treated olefin-thionophosphine sulfide adducts, of sufficiently high molecular weight, as well as their metal salts, have been found to be particularly effective as dispersant-inhibitors. When made from very high molecular weight olefin polymers, the additives can also possess V.I. (viscosity index) improving ability.

DESCRIPTION OF THE INVENTION

In accordance with the invention, compounds useful as lubricating oil additives and additive precursors are readily formed in high yields by heating an olefin with a dimeric thionophosphine sulfide. While is not intended that this invention be limited by any theory, it is believed that the reaction of an olefin, such as polyisobutylene, with a thionophosphine sulfide, as shown by equation (1) affords hydrogen sulfide and cyclic bis(-phosphinodithioic acid) anhydrides (IB) and/or (IA) wherein one of the R groups in (IA) is now an alkylidene or aralkylidene group.

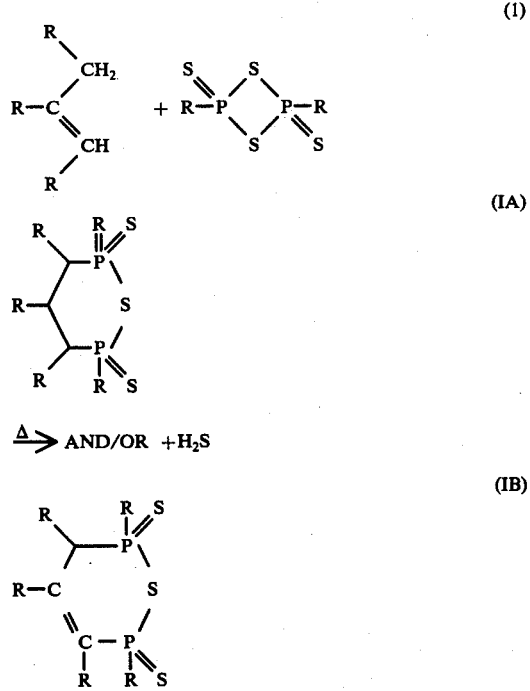

The formation of isomers (IA) and/or (IB) appears to be governed by a combination of factors associated with the reaction conditions and/or the stereoelectronic properties of the reactants and products. Thus, when a simple, unhindered olefin like 2-methyl-1-tridecene is reacted with methylthiophosphine sulfide, the exo isomer (II) appears to be the main product as shown by the following equation (2).

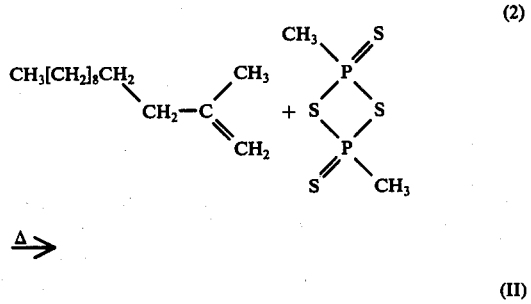

-continued

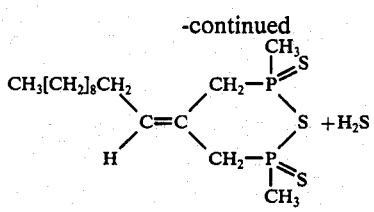

However, when the olefin reactants bear sterically demanding groups like t-alkyl groups, endo isomer (IB) predominates. For example, when either 2,4,4-trimethyl-1-pentene (diisobutylene-1), or 2,4,4-trimethyl-2-pentene (diisobutylene-2), is reacted with methylthionophosphine sulfide, the endo-isomer (III) is the predominant product as shown by equation (3).

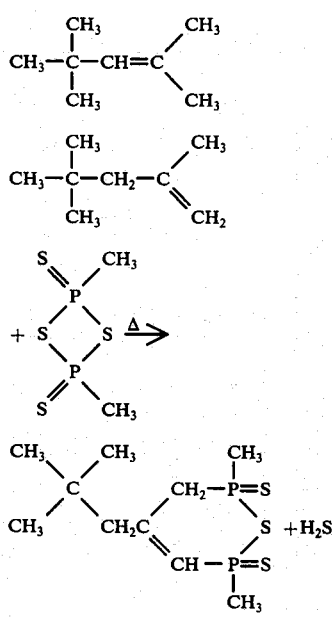

The Olefin Reactant

With respect to the olefin reactant, it is within the contemplation of the invention to use olefins ranging from short chain olefins having at least 6, preferably at least 12, carbon atoms and a single double bond, up to long chain polymers with a number of isolated double bonds.

Illustrative of short chain aliphatic monoolefins which may be used in accordance with the instant invention are octene-1, octene-2, octene-3, 2-methyl-1-octene, 2-methyl-2-octene, 3-methyl-1-octene, decene-1, dodecene-1,2,4,4-trimethyl-1-pentene, 2,4,4-trimethyl-2-pentene, 2,4-dimethyl-1-pentene, 2-methyl-1-tridecene, methallylbenzene (2-methyl-3-phenyl-1-propene), 2-methyl-1-propene, tetrapropylene, triisobutylene, etc.

Another group of useful short chain olefins are the cyclic terpenes of the formula: $C_{10}H_{16}$ such as α-pinene, β-pinene, carene, camphene, bornylene, etc.

In general, the short chain hydrocarbon olefins, e.g., those having about 8 to 50, e.g., 12 to 20, carbon atoms and having usually a single double bond, may be used to form antioxidant additives of the invention. On the other hand, the long chain hydrocarbon olefins having 50 or more carbon atoms per double bond, will generally be used to prepare additives primarily useful as sludge dispersants.

Particularly useful long chain hydrocarbon olefins for preparing the aforesaid sludge dispersants include the polymers comprising a major amount by weight of $C_2$ to $C_5$ monoolefins, e.g., ethylene, propylene, butylene, isobutylene and pentene. The polymers can be homopolymers such as polyisobutylene, as well as copolymers of two or more such olefins, such as copolymers of ethylene and propylene, butylene and isobutylene, propylene and isobutylene, etc. Still other copolymers that can be used include those in which a minor molar amount, e.g., 1 to 20 mol %, of the monomers in the copolymer is a $C_4$ to $C_{18}$ non-conjugated diolefin, e.g., a copolymer of isobutylene and butadiene, or a copolymer of ethylene, propylene and 1,4-hexadiene.

The polymers will usually have number average molecular weights within the range of about 400 and about 100,000, or more usually between about 800 and about 20,000. Particularly useful olefin polymers for making dispersants have number average molecular weights within the range of about 900 and about 3,000 with approximately one double bond per polymer chain. An especially valuable starting material for a highly potent dispersant additive made in accordance with this invention is polyisobutylene having a number average molecular weight in the range of about 1900 to about 2300, e.g., as determined by Vapor Pressure Osmometry.

Especially useful when it is desired that the dispersant additives also possess viscosity index improviding properties are 10,000 to 100,000 number average molecular weight polymers. An especially preferred example of such a V. I. improving polymer is a copolymer of about 30 to 85 mole % ethylene, about 15 to 70 mole % $C_3$ to $C_5$ mono-alpha-olefin, preferably propylene, and 0 to 20, e.g., 2 to 15, mole % of a $C_4$ to $C_{14}$ non-conjugated diene.

The ethylene-propylene V.I. improving copolymers or terpolymers are the more important ones, and are usually prepared by Ziegler-Natta synthesis methods, e.g., U.S. Pat. Nos. 3,551,336; 3,522,180 and 3,598,738. Some of these copolymers and terpolymers per se, are commercially available, such as VISTALON®, an elastomeric terpolymer of ethylene, propylene and 5-ethylidene-2-norbornene, marketed by Exxon Chemical Co., New York, N.Y. and NORDEL®, a terpolymer of ethylene, propylene and 1,4-hexadiene marketed by E. I. duPont DeNemours & Co.

The Dimeric Thionophosphine Sulfide (TPS) Reactant

In accordance with the invention, the dimeric thionophosphine sulfide reactant may be characterized by the formula:

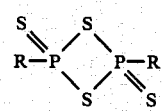

wherein R represents a $C_1$ to $C_{18}$ organic group, usually alkyl, cycloalkyl or aryl groups. In general, the alkyl groups may have from 1 to 18 carbon atoms. The cycloalkyl groups will have 6 to 18 carbons. The aryl groups may have a total of from about 6 to about 18 carbon atoms and include alkyl, or other substituents such as OH groups on the aryl group. Exemplary of alkyl and cycloalkyl substituents are methyl, ethyl, isopropyl, ethyl, isopropyl, butyl, hexyl, octyl, decyl, dodecyl, tetradecyl, cetyl, octadecyl, cyclohexyl, cyclooctyl, bicyclooctyl, etc. Representative of suitable aryl substituents are phenyl, tolyl, xylyl, anisyl, naphthyl, thienyl, 3,5-bis-t-butyl-4-hydroxy-phenyl etc.

The thionophosphine sulfides are known in the art and can be prepared by conventional methods such as from phosphorus pentasulfide and an unsaturated hydrocarbon, e.g., an aromatic hydrocarbon such as anisole, which is particularly preferred; from phosphorothioic dichlorides and $H_2S$ [see P.E. Newallis, et al, J. Organic Chem. 27, 3829 (1962)]; from primary phosphines and sulfur or sulfur monochloride [See E. Flück and H. Binder, Z. Anorg. Allg. Chemmie, 354, 113 (1967)].

Illustrative thionophosphine sulfides used in the working examples of the present invention are methylthionophosphine sulfide, p-anisylthionophosphine sulfide and 3,5-bis(t-butyl)-4-hydroxyphenylthionophosphine sulfide.

Reaction Conditions To Make The Adduct

High product yields are obtainable when equimolar amounts of olefin and dimeric thionophosphine sulfide, e.g., one mole of monoolefin and one mole of the sulfide, are mixed and heated in the temperature range of about 100° C. to about 250° C. Although not usually necessary, it is sometimes convenient to use an inert solvent or diluent in the reaction to facilitate mixing of the reactants. Typically, the thionophosphine sulfide and a suitable olefin or olefin polymer or copolymer, are combined in a reactor containing an inert solvent such as xylene, chlorobenzene, dichlorobenzene, trichlorobenzene, decane, neutral mineral lubricating oil, or another inert medium, or without a diluent, and heated gradually to a temperature in the range 100°-250° C. not substantially exceeding the boiling point of the olefin reactant. The reaction between the olefin and the dimeric thionophosphine sulfide is normally conducted under anhydrous conditions, preferably in a nonoxidizing atmosphere, e.g., nitrogen, and under atmospheric pressure to allow for the removal of the $H_2S$, a by-product produced. However, under special conditions, pressure higher than atmospheric can be employed.

Since one molecule of dimeric thionophosphine sulfide is believed to combine with one olefin in unsaturation, e.g., one molecule of monoolefin, to afford the cyclic bis (phosphinodithioic acid) anhydride selectively even when excess olefin is used, the preferred stoichiometry is 1 to 1 thionophosphine sulfide to olefin. However, slightly excess amounts of olefin may be used to facilitate reaction. For example, for olefin polymers with about one double bond per chain, such as polyisobutylene, the amount of thionophosphine sulfide used will usually be about 0.8 to 1 mole per mole of olefin polymer. In the case of 1900 to 2300 molecular weigh polyisobutylene, it is advantageous to use from about 0.9 to 1.0 mole of thionophosphine sulfide permole of polyolefin. In the case of high molecular weight polymers, such as those of ethylene, propylene and a diene, it is preferred to use about 0.05 to 1.0, e.g., 0.5 to 1.0, mole of thionophosphine sulfide per mole of diene monomer component (e.g., 5-ethylidene-2-norbornene or 1,4-hexadiene). Ordinarily, it is preferred to employ a proportion of thionophosphine sulfide that will react completely with the hydrocarbon so that no purification of the reaction product will be required before using in oil or fuel, or before proceeding with reaction of the resulting adduct with a polyamine, aziridine, phosphine or zinc salt reagent.

Completion of reaction can be determined by spectral assay or cessation of $H_2S$ evolution. A convenient procedure for assessing completion of the reaction of polyolefins with thionophosine sulfides is to use what is known as the White Spirit Test, which involves mixing one volume of the reaction mixture with 3 to 6 volumes of hexane. If a clear solution results, with no detectable turbidity, after about 15 minutes, the reaction is virtually complete.

Derivatives From Olefin-Thionophosphine Sulfide Adducts

The olefin-thionophosphine sulfide adducts can be used per se as additives, or can be utilized as intermediates in the proportion of oil soluble derivative compositions having additve properties. Moreover, the unique thioanhydride structure makes the olefin-thionophosphine sulfide adducts ammenable to numerous transformations which engender a wide spectrum of ring-opened products. Thus, the adducts react with protic reagents to yield products valuable as additives or as additive intermediates. For example, hydrolysis for extended periods affords sulfur-free bis-phosphinic acids. Reaction with alcohols or thiols as shown in equation (4) affords products (IV), which can be even further treated with zinc bases or salts, amines, epoxides, or olefins to give still other useful additives:

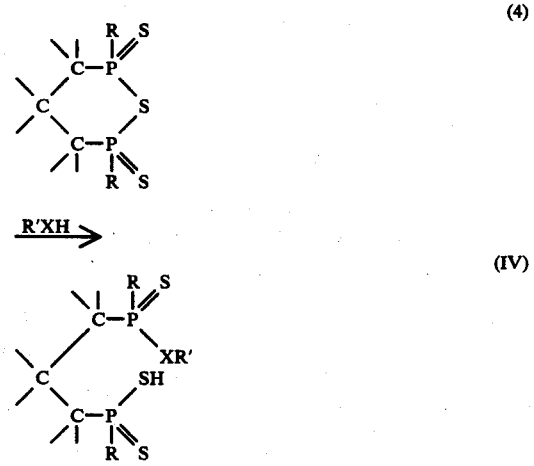

wherein R is as previously defined, R' may be the same as R, and X is oxygen or sulfur.

Of special interest is the reaction of the olefin-thionophosphine sulfide adducts with amines to give products such as V as shown in equation (5),

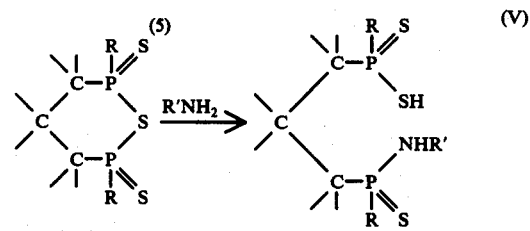

wherein R is as above; R' can be R, but preferably R' is the radical of a polyamine as will now be discussed.

Polyamine Derivatives

In particularly preferred embodiments of the invention, the olefinthionophosphine sulfide adducts are reacted with polyamines to give valuable products which have excellent dispersant-inhibitor properties. Polyamines that can be employed in preparing the reaction products of the present invention include alkylene polyamines of the general formula:

$$NH_2(CH_2)_n - [NH(CH_2)_n]_m - NH_2$$

wherein $n$ is 2 to 4 and $m$ is a number from 0 to 10. Specific compounds coming within the formula include diethylene triamine, triethylene tetramine, propylene diamine, tetraethylene pentamine, dibutylene triamine, dipropylene triamine, octaethylene nonamine, and tetrapropylene pentamine. N,N-di-(2-aminoethyl) ethylene diamine can also be used.

Other aliphatic polyamine compounds that can be used include the N-aminoalkyl piperazines of the formula:

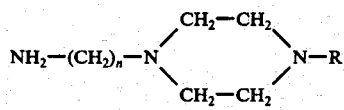

wherein n is a number 2 to 3, and R is hydrogen or an aminoalkyl radical containing 2 to 3 carbon atoms. Specific examples include N-(2-aminoethyl) piperazine, N-(2-aminopropyl) piperazine, and N,N'-di(2-aminoethyl) piperazine.

The alkylene polyamines used in the practice of this invention can be either pure alkylene amines or they can be commercial mixtures. For example, one process for preparing alkylene amines involves the reaction of an alkylene chloride such as ethylene chloride or propylene chloride, with ammonia, which results in the production of somewhat complex mixtures of alkylene amines including various piperazines. One particularly useful, low cost commercial product is a mixture of ethylene amines prepared by the reaction of ethylene chloride and ammonia and having a composition that primarily corresponds to that of a tetraethylene pentamine. One such mixture is known in the trade under the name "Polyamine H." Another similar mixture is "Polyamine 500" (PA-500) sold by Jefferson Chemical Co., New York, New York.

Still other polyamines are alkylene amino compounds including dialkylamino alkyl amines such as dimethylaminoethyl amine, dimethylamino propyl amine, methylpropylamino amyl amine, etc. These may be characterized by the formula:

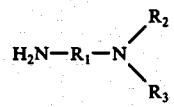

wherein $R_1$ is a $C_2$ to $C_4$ alkylene radical, e.g., an ethylene, propylene, or butylene radical, and $R_2$ and $R_3$ are generally $C_1$ to $C_5$ alkyl radicals.

In brief, the various alkylene polyamines or aliphatic polyamine compounds used in this invention can be broadly characterized as alkylene amino compounds containing from 2 to 12 nitrogen atoms, wherein pairs of nitrogen atoms joined by alkylene groups of from 2 to 4 carbon atoms.

A specific and preferred example of such polyamine derivatives is a polyisobutylene-p-anisylthionophosphine sulfide adduct, or a polyisobutylene-3,5-bis-t-butyl-4-hydroxyphenylthionophosphine sulfide adduct, treated with tetraethylene-pentamine or Polyamine H, which can give a product having outstanding dispersancy characteristics, as well as good oxidation control and satisfactory wear control, when added to a lubricating oil.

Aziridine Derivatives

Another preferred embodiment of the present invention comprises products formed by the reaction of the olefin-thionophosphine sulfide adducts with aziridines, which products, like the amine reaction products, have been demonstrated to be excellent dispersants and effective oxidation inhibitors.

The aziridines that are suitable for use in this invention can be characterized by the formula:

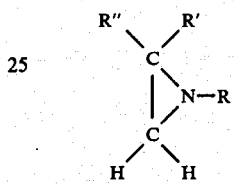

wherein each of R, R', and R" above, represents hydrogen, or an alkyl or aryl group. The alkyl group will have from 1 to 18 carbon atoms, most usually about 1 to 12 carbon atoms. The aryl groups will have from about 6 to 12 carbon atoms. Preferably R, R', and R" are either hydrogen or alkyl. A particularly suitable aziridine is ethylenimine wherein each of R, R', and R" in the above formula is hydrogen. Other representative aziridines include the 1-alkyl derivatives or 1-aralkyl derivatives, i.e., where R is alkyl or aralkyl and each of R' and R" is hydrogen, e.g., 1-methyl, 1-ethyl, 1-butyl, 1-cyclohexyl, 1-benzyl, 1-octadecyl, or 1-phenethyl aziridine; 1-substituted alkyl groups having additional functional groups on the alkyl chain such as 1-(carboalkoxy-alkyl), 1-(2-hydroxyethyl), 1-cyanoethyl, 1-(omega-aminoalkyl) aziridine, etc.; 2-alkylaziridines, i.e., where R' is alkyl and R and R" are hydrogen, e.g., 2-methyl, 2-ethyl, 2-butyl, 2-octadecyl-, or 2-benzylaziridines; and aziridines having two substituents, such as 1,2-dimethyl-, 2,2-dimethyl-, 1-methyl-2-phenyl-, 1-tert-butyl-2-phenyl-, and 2,3-dimethyl aziridine.

Phosphine Derivatives

In yet another preferred embodiment of the invention, the olefinthionophosphine sulfide adducts are reacted with trialkyl phosphines ($R_3P$) to yield useful antioxidants. The preferred trialkylphosphine according to the instant invention is trioctylphospine, but other suitable phosphine reactants include uniform or mixed trialkyl phosphines having 4 to 18 carbon atoms in the alkyl group, including nitrogen substituted alkyl groups, such as tributyl, tridecyl, and tris (2-cyanoethyl) phosphines.

General Process Conditions to Make the Derivatives

In the reactions of the olefin-thionohosphine sulfide adduct, the ring-opening agent (e.g., amine, imine, phosphine etc.) can be added to the adduct as such, or diluted in a suitable inert solvent such as pentane, hexane, tetrahydrofuran, diethyl ether, etc. The use of a solvent helps to moderate large scale reactions and also aids in mixing. A convenient solvent is a lubricating oil fraction which has the advantage of thereby forming an additive concentrate which can easily be later blended into a finished lubricating oil composition. Typically equal volumes of solvent and adduct will be used. Generally, the reaction temperature will be ambient temperature although temperatures between about 0° C and about 100° C can be used. Occasionally, the ring opening reaction is exothermic so that external cooling will be applied to maintain a desired reaction temperature. The derivative forming reactions will normally be conducted under atmospheric pressure, although pressures higher than atmospheric can be employed. Reactions will normally take about 0.5 to 30 hours, usually 1 to 4 hours, although in some instances as much as 30 hours or more, may be required to ensure that substantially all of the reagent has been incorporated into the product. In the case of exothermic reactions, the reaction can be monitored by determining when no more heat is evolved in the reaction.

Usually in the range of about 0.1 to 0.5 mole of polyamine can be reacted per atom of phosphorus in the olefin-thionophosphine sulfide adduct, depending of course, on the number of amino groups in the polyamine. About 0.5 to 1.0 moles of the aziridine per atom of phosphorus will be used, while 0.5 mole of phosphine will be usually reacted per atom of phosphorus.

At the end of the reaction, the reaction product can be freed of any low boiling components (if present), by heating the product under vacuum. This will also serve to remove the more volatile solvent is such are used, as well as any other volatile components desired to be removed from the product. Alternatively, the reaction product of the adduct, e.g., with polyamine or aziridine, in the form of its solution in a suitable solvent such as hexane, or cyclohexane, or a solvent neutral mineral lubricating oil, can be subjected to a solvent wash with an alcohol such as methanol, or ethanol, or a water-methanol mixture, which tends to further improve the efficacy of the resulting dispersant by removing sediment-forming components or sludge-forming components, as well as less effective fractions of the disperant additive. In other cases, the process can be simplified by carrying out the reaction of the adduct with other agents, in a mineral lubricating oil. The resulting product can then be used as an oil additive concentrate without further purification.

Metal Derivatives

Another particular preferred embodiment of the invention involves the further reaction of the olefin-thionophosphine sulfide, or its derivatives, with a metal salt of a $C_1$ to $C_{18}$ fatty acid or a metal alcoholate of a $C_1$ to $C_{18}$ monohydric alcohol. The salts or alcoholates may be of such heavy metals as zinc, cadmium, nickel, lead, etc. Preferably, the metal alcoholate is of a lower fatty acid of from 1 to 4 carbon atoms, or of a lower alcohol of from 1 to 4 carbon atoms, to facilitate the removal of the fatty acid or alcohol generated in this reaction. Zinc salts or zinc alcoholate are most preferred. These include zinc acetate, zinc formate, zinc ethoxide, zinc isopropoxide, etc. The reaction can be conducted at ambient temperatures, or at slightly elevated temperatures, e.g., 30° to 100° C., and can be conducted simply by adding the metal salt or metal alcoholate to the neat product or to the product dissolved in a suitable solvent such as tetrahydrofuran. The amount of metal alcoholate or carboxyl used can range from about 0.01 to about 0.5 mole equivalent of metal per atom of phosphorus in the adduct or the polamine or aziridine-treated olefin-thionophosphine sulfide. Preferably, between about 0.05 to 0.5 mole equivalent of metal salt is used per atom of phosphorus.

Lubricant and Fuel Compositions

The oil soluble additives of this invention may be employed in concentrations ranging from about 0.001 to about 10 weight percent in oleaginous compositions ranging from gasoline fractions through middle distillate fuel oils and lubricating oils.

In lubricating oil compositons, about 0.1 to about 10, e.g., 0.1 to 5, weight percent additive will ordinarily be used. The lubricating oils include not only mineral lubricating oils, but synthetic lubricating oils also. The mineral lubricating oils include those derived from the ordinary paraffinic, napthtenic, asphaltic, or mixed base mineral crude oils by suitable refining methods. Synthetic hydrocarbon lubricating oils may also be employed, as well as nonhydrocarbon synthetic oils, including dibasic acid esters such as di-2-ethyl hexyl sebacate, carbonate esters, phosphate esters, halogenated hydrocarbons, polysilicones, polyglycols, glycol esters such as $C_{13}$ oxo acid diesters of tetraethylene glycol, and complex esters, as for example the complex ester formed by the reaction of 1 mole of sebacic acid with 2 moles of tetraethylene glycol and 2 moles of 2-ethyl hexanoic acid.

The additives of this invention can also be employed in middle distillate petroleum fuels for inhibiting corrosion and/or the formation of sludge and sediment in such fuels. Concentration ranges of from about 0.002 to about 2 weight percent, or more generally from about 0.005 to about 0.2 weight percent will usually be employed. Petroleum distillate fuels boiling in the range of from about 300° to about 900° F. are contemplated. Typical of such fuels are No. 1 and No. 2 fuel oils that meet ASTM Specification D-396-48T, diesel fuels qualifying as Grades 1D, 2D and 4D of ASTM Specification D-975-51T, various jet engine fuels and gasoline.

In either the fuel or lubricant compositions, other conventional additives may also be present, including dyes, pour point depressants, anti-wear agents, e.g., tricresyl phosphate, zinc dialkyl dithiophosphates of 3 to 8 carbon atoms, antioxidants such as phenyl-alpha-naphthylamine, tert. octylphenol sulfide, bis-phenols such as 4,4'-methylene bis(2,6-di-tert.-butylphenol), viscosity index improvers such as polymetacrylates, polyisobutylene, alkyl fumarate-vinyl acetate copolymers, and the like, as well as other dispersants or detergents.

Oil concentrates containing 10 to 65 wt. T, e.g., 10 to 45 wt. %, of the additive, dissolved in mineral oil, usinga lubricating oil, may be prepared for ease of handling.

DETAILED DESCRIPTION OF THE PREFERRED EMBODIMENTS

The following Examples will serve to illustrate the processes and compounds of this invention and include preferred embodiments of the invention.

Following are some of the abbreviations used in Examples.

TPS is dimeric thionophosphine sulfide.

PIB is polyisobutylene.

PIB-460 is polyisobutylene of about 460 mol. wt.
PIB-920 is polyisobutylene of about 920 mol. wt.
PIB-2300 is polyisobutylene of about 2300 mol. wt.
PIB-12,000 is polyisobutylene of about 12,000 (Staudinger) mol. wt.
TPS-A, or p-anisyl-TPS is p-anisylthionophosphine sulfide having the structure:

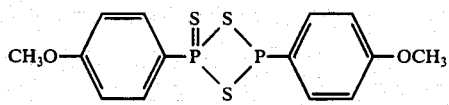

TPS-B is 3,5-bis-t-butyl-4-hydroxyphenyl thionophosphine sulfide having the structure:

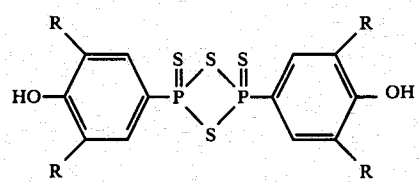

wherein R = t-butyl.
S150 N is a solvent neutral mineral lubricating oil having a viscosity of about 150 S.U.S. at 100° F.
THF is tetrahydrofuran
EI is ethylenimine
TEPA is tetraethylene pentamine
PAM is Polyamine H
TOP is trioctylphosphine
SIB is a Sludge Inhibition Bench test
"Anal. Calc'd" is the analysis calculated for a given structure in terms of wt.% C, H, P and S.
"Found" is the result of actual chemical analysis.
Mol. wt. is number average molecular weight as determined, for example, by Vapor Pressure Osmometry unless otherwise noted.

Examples 1–4 illustrate the preparation and identification of short chain olefin-thionophosphine sulfide adducts of this invention and support the reaction mechanisms and products previously postulated.

EXAMPLE 1

Part A

A mixture of 22.4 g. diisobutylene-2 (0.2 mol.), 22.0 g methyl-thionophosphine sulfide (0.1 mol.) and 100 ml. chlorobenzene, was heated to reflux in a 500 ml. round-bottom flask equipped with reflux condenser and magnetic stirrer. Refluxing overnight gave a clear solution which upon cooling to 25° C crystallized out 1.0 g. of unreacted thionophosphine sulfide which was removed by filtration. Then, an equal volume of n-hexane was added and 20.0 g. of white solid crystallized from the solution and was removed by filtration. Upon cooling in an acetone-Dry Ice bath, the filtrate gave 8.1 g. of additional crystals which were filtered off.

The 20.0 g. and 8.1 g. batches of crystals were combined and recrystallized to obtain a sharper separation of these two fractions. Specifically, the combined batches were dissolved in refluxing benzene. Hexane was then slowly added to the boiling benzene solution until the boiling mixture became slightly cloudy thereby indicating a fraction was ready to precipitate. The heat was turned off, and on slight cooling a first solid fraction crystallized out and was filtered off. The filtrate was allowed to cool to room temperature, and a second solid fraction crystallized out, which was also removed by filtration. Melting point determinations showed said first solid fraction melted at 168°–169° C., and said second solid fraction melted at 119°–120° C. Proton and carbon-13 nmr (nuclear magnetic resonance) spectral analyses indicated that the two crystalline products, i.e., said first and second solid fractions were the cis- and trans-isomers of 2-neopentylpropenylene bis(methylphosphinodithioic acid) anhydride (III).

Anal. Calc'd for $C_{10}H_{20}P_2S_3$: C, 40.25; H, 6.76; P, 20.76; S, 32.34. Found: C, 40.63; H, 6.66; P, 20.31; S, 33.00.

Part B

Repetition of the above experiment with diisobutylene-1 also afforded a mixture of the cis and trans isomers of 2-neopentylpropenylene bis (methylphosphinodithioic acid) anhydride (III) in high yields.

EXAMPLE 2

A mixture of 8.0 g. of 2-methyltridecene-1 and 4.4 g. of methylthionophosphine sulfide was heated at 200° C for 2 hours. Upon cooling, the reaction mixture was diluted with an equal volume of n-hexane and a white solid separated from solution. The solid product weighed 5.5 g. and melted at 74°–75° C. The spectral data were consistent with the proposed 2,6-bisthiono-2,6-dimethyl-4-n-undecylidene-1,2,6-thiadiphosphorinane structure (II). Anal. Calc'd for $C_{16}H_{32}P_2S_3$:

C, 50.23; H, 8.43; P, 16.19; S, 25.14. Found: C, 50.24; H, 8.44; P, 16.54; S, 26.0.

EXAMPLE 3

Part A

A mixture of 4.4 g. of methylthionophosphine sulfide and 7.0 g. of methyllylbenzene (2-methyl-3-phenyl-1-propene) was heated together at 190° C. for 2 hours. Upon cooling the reaction mixture to 25° C., a solid product separated from the solution. The product was isolated by filtration and weighed 5 5 g. after drying. The white solid showed a melting point of 161°–162° C. and spectral features consistent with a 2,6-bisthiono-1,6-dimethyl-4-benzylidene-1,2,6-thiadiphosphorinane structure.

Anal. calc'd for $C_{12}H_{26}P_2S_3$: C, 45.26; H, 5.06; S, 30.21. Found: C, 45.48; H, 5.13; P, 19.32; S, 30.80.

Part B

When the isomeric olefin, 2-methyl-1-phenyl-1-propene, was reacted with dimeric methylthiophosphine sulfide in the same manner as above, the identical product, 2,6-bis-thiono-2,6-dimethyl-4-benzylidene-1,2,6-thiadiphosphorinane was obtained in high yield.

EXAMPLE 4

A mixture of 39.6 g. (0.3 mol) of 2-methyl-3-phenyl-1-propene (methallyl benzene) and 60.6 g. (0.15 mol) of p-anisyl-thionophosphine sulfide (p-anisyl-TPS) was heated at 175° C. for 2 hours. Addition of 100 ml. toluene to the cooled reaction mixture caused solids to separate from solution. Isolation by filtering gave 3 g. of the p-anisyl-TPS starting material. The supernatent, upon addition of a large volume of n-pentane (ca. 3 liters), gave a white precipitate amounting to 67 g. dried product. Repurification by this procedure afforded a solid which showed spectral and analytical data consonant with the proposed thiadiphosphorinane structure.

Anal. calc'd for $C_{24}H_{24}O_2P_2S_3$: C, 57.35; H, 4.81; P, 12.33; S, 19.14. Found: C, 55.82; H, 4.95; P, 12.28; S, 20.80; 19.90.

Examples 5 to 18 which follow demonstrate a long chain monoolefin polymer, i.e., polyisobutylene, reacted with the dimeric thionophosphine sulfide.

EXAMPLE 5

A 1,810 g. portion of polyisobutylene of about 920 number average molecular weight (PIB-920) was placed in a reactor and heated to 170° C. with stirring in a nitrogen atmosphere. Then over a period of 30 minutes, 613.3 g. of p-anisyl thionophosphine sulfide (TPS-A) was added, and the mixture was subsequently heated to 230°–235° C. Reaction was complete in about 4 hours as determined by the aforementioned positive White Spirit Test. Analysis of the product showed a phosphorus content of 3.88 weight percent and a sulfur content of 6.78 weight percent.

EXAMPLES 6 to 18

In a manner similar to that described in Example 5, various polyisobutylenes (PIB) of differing molecular weights were reacted with p-anisyl thionophosphine sulfide (TPS-A) and 3,5-bis-t-butyl-4-hydroxylphenylthionophosphine sulfide (TPS-B) under various conditions. A spectrum of adducts were obtained from the reaction of these two dimeric thionophosphine sulfides, i.e., TPS-A and TPS-B, with the undiluted polyisobutylenes at about 200°–235° C. for several hours until completion of the reaction was ascertained by observing a positive White Spirit Test. All the reaction products were analyzed as is, except for Example 8, where the reaction product was first washed with methanol before analysis.

The reactants, amount of reactants used, and analyses of the products, of Examples 5 to 18 are summarized in Table I, which follows:

TABLE I
POLYISOBUTYLENE-THIONOPHOSPHINE SULFIDE REACTION PRODUCTS

| | PIB | | TPS | | Analyses* | |
|---|---|---|---|---|---|---|
| Ex. | Mol. Wt. | Grams | Type | Grams | %S | %P |
| 5 | 920 | 1810 | A | 613.3 | 6.78 | 3.88 |
| 6 | 920 | 100 | A | 32 | 5.79 | 4.46 |
| 7 | 2300 | 200 | A | 20 | 2.88 | 1.66 |
| 8 | 920 | 100 | A | 20.2 | — | 2.29** |
| 9 | 460 | 42 | A | 32 | — | 4.60 |
| 10 | 920 | 845 | A | 274.7 | 6.24 | 3.86 |
| 11 | 2300 | 1054 | A | 169.6 | — | 1.22 |
| 12 | 920 | 470 | B | 120.4 | 3.50 | 2.22 |
| 13 | 920 | 1041 | B | 209 | 6.00 | 3.80 |
| 14 | 2300 | 1041 | B | 209 | 1.96 | 1.10 |
| 15 | 2300 | 1034 | B | 210 | 3.24 | 1.80 |
| 16 | 12,000≠ | 300 | A | 8.08 | 0.46 | 0.32 |
| 17 | 12,000≠ | 300 | A | 6.06 | 0.42 | 0.24 |
| 18 | 12,000≠ | 300 | A | 4.04 | 0.36 | 0.18 |

*Analyses on neat products, i.e., products per se without any diluent oil.
**Washed with methanol before analysis
≠ Viscosity average mol. wt. (Staudinger).

Examples 19 to 28 illustrate the preparation of ethylenimine treated olefin-thionophosphine sulfide adducts in accordance with this invention.

EXAMPLE 19

Fifty grams of p-anisyl TPS-polyisobutylene adduct, prepared by interacting 100 g. of polyisobutylene (PIB-920) with 20.2 g. p-anisyl TPS in the general manner described in Example 5, were diluted with an equal weight of neutral oil (S 150N) and charged into a reactor. After adding 100 ml. of tetrahydrofuran (THF), 15 grams of ethylenimine (EI) were gradually added to the stirred solution at 25° C. The reaction mixture, after being stirred several hours at 20° C was rotoevaporated, to remove the THF solvent at 60°–90° C. for 2-3 hours. The product, a viscous amber liquid, was dissolved in an equal amount of S 150N to form an oil concentrate which analyzed for 1.04% phosphorus, 1.66% sulfur and 0.67% nitrogen.

EXAMPLES 20 to 28

In the manner similar to that described in Example 19, a variety of TPS-polyisobutylene adducts were treated with an excess of ethylenimine (EI).

Analytical data and the reactants for these EI-treated PIB-TPS adducts of Examples 19 to 28 are summarized in Table II which follows:

TABLE II
EI-TREATED PIB-TPS ADDUCT

| | Adduct of | | Analysis of EI-Treated Adduct* | | |
|---|---|---|---|---|---|
| Example | PIB, Mol. Wt. and TPS | | %N | %P | %S |
| 19 | 920 | A | .67 | 1.04 | 1.66 |
| 20 | 920 | A | 1.85 | 1.87 | 2.95 |
| 21 | 920 | B | 1.43 | 1.19 | 1.89 |
| 22 | 2300 | A | 1.22 | 1.10 | 1.60 |
| 23 | 2300 | A | 0.65 | 0.56 | 0.83 |
| 24 | 2300 | A | .99 | 1.16 | 1.68 |
| 25 | 2300 | B | 1.30 | 1.20 | 1.90 |
| 26 | 2300 | B | 0.70 | 0.53 | 0.89 |
| 27 | 12,000* | A | 0.12 | 0.19 | 0.31 |
| 28 | 12,000* | A | 0.12 | 0.04 | 0.13 |

*In all cases, the analytical data are for the 50% active ingredient in S 150N.
**Staudinger mol. wt. All other mol. wts. are number average.

Example 29 illustrates the preparation of alkylenepolyamine treated olefin-thionophosphine sulfide adducts in accordance with this invention.

EXAMPLE 29

One hundred grams of polyisobutylene (PIB-920) was charged into a reactor and heated to 175° C. under a nitrogen atmosphere. To the stirred polyolefin was added 32 g. of p-anisyl TPS portionwise over a 10 minute period. Upon complete addition, the temperature was raised to 230° C., and kept at this reading until a sample of the reaction mixture gave a clear hexane solution in the White Spirit Test (about 2 hours reaction time). The reaction mixture was allowed to cool, taken up in 300 ml. of pentane and filtered. The clear solution was then treated with 5.4 g. of tetraethylenepentamine (TEPA), and the reaction mixture was stirred at 25° C. for several hours. Rotoevaporation of the mixture gave a viscous product which was diluted with an equal weight of S 150N. The diluted product analyzed for 2.27% nitrogen, 1.73% phosphorus and 2.81% sulfur.

EXAMPLES 30 to 42

In the manner similiar to that described in Example 29, a number of TPS-polyisobutylene adducts were reacted with varying amounts of polyamines and then diluted with S 150N to form oil concentrates.

Table III summarizes the reactant and analytical data for the PIB/TPS/Polyamide products of Examples 29 to 42.

TABLE III
PIB-TPS-POLYAMINE PRODUCTS

| | Adduct of | | Treated With | Analysis of Polyamine Treated Adduct* | | |
|---|---|---|---|---|---|---|
| Ex. | PIB, Mol. Wt. and TPS | | Polyamine | %N | %P | %S |
| 29 | 920 | A | TEPA | 2.27 | 1.73 | 2.81 |
| 30 | 920 | A | TEPA | 1.06 | 1.02 | 1.70 |
| 31 | 920 | A | PAM | 1.27 | 1.94 | 3.39 |

TABLE III-continued
PIB-TPS-POLYAMINE PRODUCTS

| | Adduct of | | Treated With | Analysis of Polyamine Treated Adduct* | | |
|---|---|---|---|---|---|---|
| Ex. | PIB, Mol. Wt. | and TPS | Polyamine | %N | %P | %S |
| 32 | 2300 | A | TEPA | 1.22 | 1.10 | 1.60 |
| 33 | 2300 | A | PAM | 1.31 | 0.88 | 1.62 |
| 34 | 2300 | A | PAM | 1.26 | 0.55 | 0.71 |
| 35 | 2300 | A | TEPA | 1.02 | 0.83 | 1.44 |
| 36 | 920 | B | TEPA | 1.02 | 1.83 | 2.87 |
| 37 | 920 | B | TEPA | 1.25 | 1.06 | 1.62 |
| 38 | 920 | B | PAM | 1.48 | 1.02 | 1.70 |
| 39 | 2300 | B | TEPA | 1.69 | 0.84 | 1.48 |
| 40 | 2300 | B | PAM | 1.79 | 0.84 | 1.47 |
| 41 | 12,000** | A | TEPA | 0.20 | 0.10 | 0.20 |
| 42 | 12,000** | A | TEPA | 0.11 | 0.04 | 0.13 |

*Analytical data for 50% active ingredient in S 150N.
** Staudinger mol. wt. All other mol. wts. were determined by osmometry.

Examples 43 to 56 illustrate the preparation of zinc derivatives of imine- and amine-treated olefin-thionophosphine sulfide adducts in accordance with the present invention.

EXAMPLE 43

Oil soluble-zinc-containing adducts were readily prepared via the reaction of zinc acetate with the alkylene polyamine and aziridine-treated PIB-TPS adducts.

Thus, PIB-920/p-anisyl TPS adduct in 100 ml. of tetrahydrofuran was treated with 15 ml. of ethylenimine (EI), at 25° C. After stirring the mixture overnight, the reaction mixture was rotoevaporated at 60°-90° C. for several hours. The resulting viscous product analyzed for 0.67% nitrogen, 1.04% phosphorus and 1.66% sulfur. The resulting product was dissolved in 100 ml. THF and was then treated with 3.86 grams of zinc acetate dihydrate and refluxed for several hours. The mixture was allowed to stir overnight at 25° C. Thereafter, the reaction mixture was concentrated by rotoevaporation at 90° C. for several hours. The residue was taken up in hexane and filtered to remove any solids. After a final rotoevaporation, the viscous product was dissolved in S 150N to form a 50% concentrate which analyzed for 0.75%, N, 1.00% P, 1.62% S, and 1.00% Zn.

EXAMPLE 44

To a stirred solution of 100 g. of PIB-2300/p-anisyl TPS in 100 ml. THF was added 6.0 g. of tetraethylenepentamine (TEPA) at 25° C. Thereafter, 3.86 g. of zinc acetate dihydrate were added and allowed to stir until dissolution of the ZnAc$_2$ was complete. Rotoevaporation at 60°-90° C. for several hours gave a clear, viscous product which was then dissolved in S 150N to form a 50% concentrate which analyzed for 1.18% zinc (50% active ingredient in S 150N).

EXAMPLES 45 to 56

In the manner similar to that illustrated in Examples 43 and 44, a wide spectrum of amine and imine-treated PIB/TPS adducts were converted to the zinc derivatives using zinc acetate dihydrate and used to form 50% concentrate in S 150N.

Elemental analyses for the products of Examples 43 to 56, along with the reactants are summarized in Table IV.

TABLE IV
ANALYTICAL DATA FOR PIB-TPS-EI-Zn AND PIB-TPS-POLYAMINE-Zn Products

| | Adduct of PIB, | | Adduct Treated | Analysis of Product* | | | |
|---|---|---|---|---|---|---|---|
| Ex. | Mol. Wt. | and TPS | With | %N | %P | %S | %Zn |
| 43 | 920 | A | EI | .75 | 1.00 | 1.62 | 1.00 |
| 44 | 2300 | A | TEPA | — | — | — | 1.18 |
| 45 | 920 | A | EI | 1.85 | 1.89 | 2.95 | 1.91 |
| 46 | 920 | A | TEPA | 1.37 | 1.84 | 2.91 | 1.24 |
| 47 | 920 | A | PAM | 1.62 | 1.84 | 2.98 | 2.11 |
| 48 | 920 | A | EI | 0.75 | 1.00 | 1.62 | 1.00 |
| 49 | 920 | B | EI | 1.48 | 1.26 | 1.90 | 1.04 |
| 50 | 920 | B | TEPA | 0.90 | 1.74 | 2.78 | 1.91 |
| 51 | 920 | B | TEPA | 1.23 | 1.04 | 1.68 | 1.12 |
| 52 | 920 | B | PAM | 1.18 | 1.03 | 1.62 | 1.08 |
| 53 | 2300 | A | EI | 0.52 | 0.32 | 0.92 | 0.57 |
| 54 | 2300 | B | PAM | 1.54 | 0.83 | 1.45 | 1.07 |
| 55 | 2300 | B | PAM | 1.16 | 0.51 | 0.88 | |
| 56 | 2300 | A | TEPA | 1.12 | 0.92 | 1.51 | 0.65 |

*Analytical data for 50% active ingredient in S 150N.

Examples 57 to 63 illustrate the preparation of trialkylphosphineolefin-thionophosphine sulfide adducts in accordance with the present invention

EXAMPLE 57

A p-anisyl TPS/polyisobutylene adduct was prepared from 1,810 g. of PIB-920 and 613.3 g. of p-anisyl TPS. Fifty grams of the adduct, as a 50 wt. % solution in neutral oil (S 150N), were then treated with 22.8 g. of trioctylphosphine (TOP) and the mixture was heated at 80° C. for several hours, with stirring. Rotoevaporation of the reaction mixture at 90° C. for several hours gave a viscous product which analyzed for 3.08% phosphorus and 2.59% sulfur.

EXAMPLES 58 to 63

In the manner similar to that described in Example 57, a number of PIB/TPS adducts were treated with tri-n-octylphosphine (TOP).

Analytical data for these products of Examples 57 to 63, and the reactants, are summarized in Table V.

TABLE V
ANALYTICAL DATA FOR PIB-TPS-TRIALKYL-PHOSPHINE PRODUCTS

| | Adduct of | | Analysis of TOP-TREATED Adducts | |
|---|---|---|---|---|
| Example | PIB, Mol. Wt. | and TPS | %P | %S |
| 57 | 920 | A | 3.08 | 2.59 |
| 58 | 920 | A | 3.28 | 2.87 |
| 59 | 2300 | A | 2.36 | 2.68 |
| 60 | 920 | B | 3.10 | 2.42 |
| 61 | 920 | B | 1.82 | 1.59 |
| 62 | 2300 | B | 3.12** | 2.55** |
| 63 | 2300 | B | 1.79** | 1.67** |

*Analytical data for 50% active ingredient in S150N unless otherwise noted.
**Analytical data for neat product, i.e., undiluted product.

Example 64 illustrates zinc-treated olefin-thionophosphine sulfide adducts in accordance with the present invention

EXAMPLE 64

The TPS-A was prepared by treating 1,810 grams of polyisobutylene (PIB-920) at 185°-190° C. with 613.27 grams of p-anisylthionophosphine sulfide. The resulting mixture was heated to 230°-235° C. until a positive White Spirit Test was realized.

One thousand grams of TPS-A was dissolved in a liter of tetrahydrofuran and heated to reflux. To the refluxing solution was then added 134.5 grams of zinc acetate dihydrate, after which refluxing was continued for 7 hours. The product was filtered, concentrated by rotoevaporation for several hours and diluted with an equal amount of neutral oil (S 150N) to form a 50% concentrate. The diluted solution analyzed for 2.03% phosphorus, 2.58% sulfur and 1.38% zinc.

EXAMPLE 65

Sludge Dispersancy Test

A number of the additives of this invention were subjected to a Sludge Inhibition Bench (SIB) Test which has been found, after a large number of evaluations, to be an excellent test for assessing the dispersing power of lubricating oil dispersant additives.

The medium chosen for the Sludge Inhibition Bench Test was a used crankcase oil having an original viscosity of about 325 SUS at 100° F. that had been used in taxicabs driven generally for short trips only, thereby causing a buildup of a high concentration of sludge precursors. The oil that was used contained only a refined base oil, a viscosity index improver, a pour point depressant and zinc dialkyl dithiophosphate antiwear additive. The oil contained no sludge dispersants. The oil was obtained by drawing and refilling the crankcases of the cabs at 1000–2000 mile intervals.

The used crankcase oil, which is milky brown in color, is freed of sludge by centrifuging for 1 hour at 39,000 gravities (gs). The clear bright red supernatant oil is decanted from the insoluble sludge particles and thereby separated out. However, the supernatant oil still contains oil-soluble sludge precursors, which on heating under the conditions employed by this test, will tend to form additional oil-soluble deposits of sludge.

The sludge inhibiting properties of the additives being tested are determined by adding to portions of the supernatant used oil either 1 or 2 weight percent, on a 50% active ingredient basis, of a particular additive being tested. Comparison blends are also prepared using a standardized commercial dispersant.

Ten grams of each blend being tested is placed in a stainless steel centrifuge tube and heated at 280° F. for 16 hours in the presence of air. Following the heating, the tube containing the oil being tested is cooled and then centrifuged for 30 minutes at 39,000 gs. Any deposits of sludge that form in this step are separated from the oil by decanting the supernatant oil and then carefully washing the sludge deposits with 25 ml. of pentane to remove all remaining oil from the sludge.

The weight of the solid sludge that has been formed in the test, in milligrams, is determined by drying the residue and weighing it. The results are reported as milligrams of sludge per 10 grams of oil, thus measuring differences as small as 1 part per 10,000. The less sludge formed the more effective the additive as a sludge dispersant.

Using the above-described test, the dispersant action of additives of the present invention was compared with Comparison Dispersants A, B and C identified below.

Comparison Dispersant A (CD-A)

This was an additive concentrate of 50 wt. % mineral lubricating oil and 50 wt. % PIBSA/TEPA dispersant prepared by reaction of about 1 mole of tetraethylenepentamine (TEPA) with about 2.8 moles of polyisobutenyl succinic anhydride (PIBSA) prepared from polyisobutylene of about 920 number average molecular weight. The additive concentrate (50 wt. % active ingredient) analyzed about 1.14% nitrogen, indicating that the active ingredient contained about 2.28% nitrogen.

Comparison Dispersant B (CD-B)

This dispersant was formed by heating 150 parts by weight of $P_2S_5$ with 850 parts by weight of polyisobutylene of about 920 molecular weight (PIB-420) at 200°–220° C until a positive White Spirit Test was obtained. The resulting undiluted product analyzed for 3.3% phosphorus and 5.90% sulfur. Thereafter, 110 grams of the resulting $P_2S_5$ treated PIB-960 was condensed with 6.0 grams of ethylene diamine and diluted with S 150N to make a 50 wt. % concentrate.

Comparison Dispersant C(CD-C)

This dispersant was also a 50 wt. % concentrate in S 150N, and was similar to CD-B above, except that 110 grams of the $P_2S_5$ treated PIB-920 described above was reacted with 18.9 grams of tetraethylenepentamine (TEPA).

As noted above CD-A is a lube oil sludge dispersant representative of those in widespread use and well known in the art, e.g., see U.S. Pat. Nos. 3,272,746 and 3,172,892. CD-B and CD-C are representative of dispersants described in other prior art patents, U.S. Pat. No. 3,329,612 and British 970,880.

The SIB tests were carried out on the products of Examples 20, 23, 24, 26, 32, 34, 39, 40, 49, 53 and 56 in using 1 and 2 weight percents of said products in the test oil. In addition, similar 1 and 2 wt. % blends of CD-A, CD-B, and CD-C, were made up in the used oil. In other words, 1 and 2 wt. % of 50 wt. % concentrates were used in each case, so that the test oils contained 0.5 and 1.0 wt. % active ingredient, respectively.

The results of the aforesaid additives in the SIB test are summarized in Table VI, which follows, along with analytical data for these additives as 50% active ingredient in neutral oil.

TABLE VI

ANALYTICAL AND SIB DATA FOR INVENTIVE AND COMPARISON PRODUCTS

| | Composition | | | Analysis* | | | | SIB Test mg. Sludge/10g. Oil | | |
|---|---|---|---|---|---|---|---|---|---|---|
| Example | PIB, Mol. Wt. | TSP | Other | %N | %P | %S | %Zn | 2.0% | .0% | (Wt. % additive) |
| 20 | 920 | A | EI | 1.85 | 1.87 | 2.95 | — | 0.77 | 0.0 | |
| 23 | 2300 | A | EI | 0.65 | 0.56 | 0.83 | — | 0 | 0 | |
| 24 | 2300 | A | EI | 0.99 | 1.16 | 1.68 | — | 0 | 0 | |
| 32 | 2300 | A | TEPA | 1.22 | 1.10 | 1.60 | — | 0 | 0 | |
| 34 | 2300 | A | PAM | 1.26 | 0.55 | 0.71 | — | 0 | 0 | |
| 26 | 2300 | B | EI | 0.70 | 0.53 | 0.89 | — | 0.5 | 1.72 | |
| 39 | 2300 | B | TEPA | 1.69 | 0.84 | 1.48 | — | 0 | 1.8 | |
| 40 | 2300 | B | PAM | 1.79 | 0.84 | 1.47 | — | 0 | 3.7 | |
| 53 | 2300 | A | EI-Zn | 0.52 | 0.52 | 0.92 | 0.57 | 0 | 0 | |
| 56 | 2300 | A | TEPA-Zn | 1.12 | 0.92 | 1.51 | 0.65 | 0 | 0 | |
| 49 | 920 | B | EI-Zn | 1.48 | 1.26 | 1.90 | 1.04 | 0.8 | 2.5 | |

TABLE VI-continued
ANALYTICAL AND SIB DATA FOR INVENTIVE AND COMPARISON PRODUCTS

| | Composition | | | Analysis* | | | | SIB Test mg. Sludge/10g. Oil | | |
|---|---|---|---|---|---|---|---|---|---|---|
| Example | PIB, Mol. Wt. | TSP | Other | %N | %P | %S | %Zn | 2.0% | .0% | (Wt. % additive) |
| CD-A | — | — | PIBSA-TEPA | 1.14 | — | — | — | 2.2 | 5.2 | |
| CD-B | — | — | PSPIB-EDA | 1.05 | — | — | — | 9.4 | 11.1 | |
| CD-C | — | — | PSPIB-TEPA | 1.34 | — | — | — | 13.1 | 11.2 | |

* All analyses were on solution of 50 wt.% of S 150N and 50 wt. % actual active ingredient.

As seen near the bottom of Table VI, the PIBSA-TEPA type ashless dispersant (CD-A) having 1.14 wt. % N, at the 2 wt. % concentration gave 2.2 mg. of precipitated sludge during oxidation of the 10 g. oil sample. Making the dispersant by $P_2S_5$ treatment of the polyisobutylene and then neutralizing with polyamines, e.g., EDA or TEPA, as shown by CD-B, and CD-C, gave sludge readings of 9.4 and 13.1 mg. respectively at the 2% treat level. In contrast thereto, all the additives of the Examples were more effective in dispersing the sludge than any of the aforesaid Comparisons, i.e., CD-A, B and C.

EXAMPLE 66

Blend A (Comparison) A low ash, fully formulated 10W-30 motor crankcase lubricating oil blend was prepared by blending 6.5 weight percent of a PIBSA--TEPA type ashless dispersant additive (50% a.i.), i.e., CD-A previously described, a hydrocarbon viscosity index improver, a zinc dialkyldithiophosphate antiwear additive, a sulfurized calcium nonyl phenate and a rust preventive into a refined lubricating mineral oil base stock.

Blends B to D

The same 10W-30 formulation as above was prepared, except that in place of the 6.5 wt. % concentrate of the PIBSA-TEPA type dispersant, 6.5 wt. % of the 50 wt. % concentrate of Examples 31, 34, and 24 were used. The formulations above were then tested for antiwear ability in a Falex Wear Test and oxidation stability in a LMOT test. These tests were carried out as follows:

The Falex test was carried out in a Falex machine operating under a 500 pound load for 30 minutes and then measuring the weight loss of the brass pin to indicate the amount of wear.

The Laboratory Multiple Oxidation Test (LMOT)

This test was carried out using a 40 g. sample of the oil. In this test, 2.4 g. of iron filings, a 19 inch piece of No. 14 gauge copper wire and a sanded aluminum strip (12 × ¼ × 1/16 inch) are added as catalysts to the oil composition. Then 10 liters of air was bubbled through the sample maintained at 300° F. At the end of 120 hours, the oil was evaluated for sludge by placing a drop on a paper blotter and visually examining the paper blotter for sludge. Also, the aluminum strip is examined for varnish deposits, and the neutralization number (ASTM-D-974) of the used, i.e., oxidized, oil is determined.

The dispersants tested, and the results obtained are summarized in Table VII which follows:

TABLE VII
DISPERSANTS IN LOW ASH FOR FORMULATIONS

| Dispersant | Blend | | | |
|---|---|---|---|---|
| | A | B | D | D |
| PIBSA-TEPA (CD-A) | 6.5% | — | — | — |
| EXAMPLE 31 | — | 6.5% | — | — |
| EXAMPLE 34 | — | — | 6.5% | — |
| EXAMPLE 24 | — | — | — | 6.5% |
| Viscosity at 210° F., SUS. | 10.93 | 10.53 | 9.24 | 11.83 |
| Falex, wear, mg., | 10.7 5.4 | 3.5 | 5.6 | |
| LMOT, time to sludging, days | 6–7 | 5 | 7 | tc 7+ |

As seen by Table VII, the additives of the invention decreased the wear, and in the case of Examples 34 and 24, were about equivalent or slightly better than the PIBSA-TEPA dispersant, CD-A.

What is claimed is:

1. An oleaginous composition comprising a major amount of an oleaginous material selected from the group consisting of lubricating oil and normally liquid petroleum fuel, and a minor amount, in the range of about 0.001 to 10 wt. %, of a sludge dispersant which is the reaction product of:

I. an oil soluble olefin-thionophosphine sulfide adduct of (1) an olefin having at least six carbon atoms and at least one double bond, and (2) a dimeric thionophosphine sulfide having the structure:

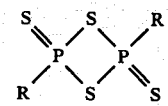

wherein, R is an organic radical selected from the group consisting of anisyl, thienyl, $C_1$ to $C_{18}$ alkyl, $C_6$ to $C_{18}$ cycloalkyl, and $C_6$ to $C_{18}$ aryl radicals which may be unsubstituted or hydroxy substituted; said adduct being formed by heating said olefin and said sulfide together, under anhydrous conditions, at a temperature in the range of about 100° to 250° C., with the evolution of $H_2S$, said olefin being selected from the group consisting of:

a. short chain hydrocarbon mono-olefin of 8 to 50 carbon atoms;

b. long chain unsaturated hydrocarbon polymers of $C_2$ to $C_5$ mono-olefins, said polymers having a molecular weight in the range of 400 to 100,000; and c. copolymers of about 30 to 85 mole % ethylene, about 15 to 70 mole % $C_3$ to $C_5$ mono-alpha olefin, and about 2 to 15 mole % of $C_4$ to $C_{14}$ non-conjugated diene; and wherein said adduct is the reaction to product of substantially equimolar proportions of said sulfide with said olefins of group (a) and group (b) above; and wherein said adduct is the reaction product formed by reacting in the range of about 0.05 to 1.0 molar proportion of said sulfide per molar proportion of said diene, when reacted with the olefin of group (c) above; with either II. a polyamine, in a relative proportion of about 0.1 to 0.5 mole of polyamine per atom of phosphorus in said adduct, said polyamine containing 2 to 12 nitrogen atoms wherein pairs of nitrogen atoms are joined by alkylene groups of 2 to 4 carbon atoms, and are selected from the group consisting of polyamines defined by the formulae:

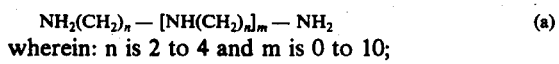

(a)

wherein: n is 2 to 4 and m is 0 to 10;

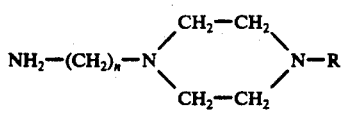

(b)

wherein $n$ is 2 to 3 and R is selected from the group consisting of hydrogen and aminoalkyl radicals of 2 to 3 carbon atoms; and

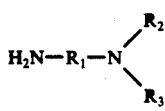

(c)

wherein $R_1$ is a $C_2$ to $C_4$ alkylene radical, and $R_2$ and $R_3$ are $C_1$ to $C_5$ alkyl radicals;

wherein a molar proportion of said adduct has been reacted, at a temperature in the range of 0° to 100° C., with said polyamine; or III. an aziridine having the formula:

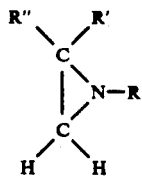

wherein each of said R, R' and R" are selected from the group consisting of hydrogen, alkyl groups of 1 to 18 carbon atoms and aryl groups of 6 to 12 carbon atoms, wherein a molar proportion of said adduct has been reacted at a temperature in the range of 0° to 100° C., with said aziridine in a relative proportion of about 0.5 to 1.0 mole of aziridine per atom of phosphorus in said adduct.

2. An oleaginous composition according to claim 1, wherein said olefin is a polymer comprising principally $C_2$ to $C_5$ monoolefin, said polymer having a molecular weight in the range of about 400 to 100,000.

3. An oleaginous composition according to claim 1, wherein said oleaginous material is mineral lubricating oil, and said olefin is polyisobutylene of about 800 to 20,000 molecular weight.

4. An oleaginous composition according to claim 3, wherein said sludge dispersant is the reaction product of said adduct and said polyamine.

5. An oleaginous composition according to claim 3, wherein said sludge dispersant is the reaction product of said adduct and said aziridine.

6. An oleaginous composition according to claim 4, wherein said reaction product is that of said adduct and said polyamine which has been further converted into a heavy metal salt by further reaction, in a relative proportion of a molar proportion of said adduct with about 0.05 to 0.5 mole equivalent, per atom of phosphorus in said adduct, of a metal reactant selected from the group consisting of zinc, cadmium, nickel and lead salts of: (1) $C_1$ to $C_{18}$ fatty acid, and (2) alcoholates of $C_1$ to $C_{18}$ monohydric alcohol.

7. An oleaginous composition according to claim 5, wherein said reaction product is that of said adduct and said aziridine which has been further converted into a heavy metal salt by further reaction, at a temperature up to about 100° C., of a molar proportion of said adduct with about 0.05 to 0.5 mole equivalent, per atom of phosphorus in said adduct, of a metal reactant selected from the group consisting of zinc, cadmium, nickel and lead salts of: (1) $C_1$ to $C_{18}$ fatty acid, and (2) alcoholates of $C_1$ to $C_{18}$ monohydric alcohol.

8. An oleaginous composition according to claim 4, wherein said dimeric thionophosphine sulfide is selected from the group consisting of p-anisyl thionophosphine sulfide and 3,5-bis-t-butyl-4-hydroxyl-phenylthiophosphine sulfide, and said polyamine is tetraethylene pentamine.

9. An oleaginous composition according to claim 5, wherein said aziridine is ethyleneimine wherein each of R, R' and R" are hydrogen, and wherein said dimeric thionophosphine sulfide is selected from the group consisting of p-anisyl thionophosphine sulfide and 3,5-bis-t-butyl-4-hydroxyl phenylthionophosphine sulfide.

10. An oil concentrate comprising 35 to 90 wt. % of a mineral oil and 10 to 65 wt. % of a sludge dispersant which is the reaction product of:

I. an oil soluble additive comprising principally olefin-thionophosphine sulfide adduct of (1) an olefin having at least six carbon atoms and at least one double bond, and (2) a dimeric thionophosphine sulfide having the structure:

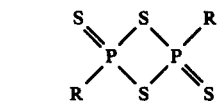

wherein, R is an organic radical selected from the group consisting of anisyl, thienyl, $C_1$ to $C_{18}$ alkyl, $C_6$ to $C_{18}$ cycloalkyl, and $C_6$ to $C_{18}$ aryl radicals which may be unsubstituted or hydroxy substituted; said adduct being formed by heating said olefin and said sulfide together, under anhydrous conditions, at a temperature in the range of about 100 to 250° C., with the evolution of $H_2S$, said olefin being selected from the group consisting of:

a. short chain hydrocarbon mono-olefin of 8 to 50 carbon atoms;

b. long chain unsaturated hydrocarbon polymers of $C_2$ to $C_5$ mono-olefins, said polymers having a molecular weight in the range of 400 to 100,000; and c. copolymers of about 30 to 85 mole % ethylene, about 15 to 70 mole % $C_2$ to $C_5$ monp-alpha olefin, and about 2 to 15 mole of $C_4$ to $C_{14}$ non-conjugated diene; and wherein said adduct is the reaction product of substantially equimolar proportions of said sulfide with said olefins of group (a) and group (b) above; and wherein said adduct is the reaction product formed by reacting in the range of about 0.05 to 1.0 molar proportion of said sulfide per molar proportion of said diene, when reacted with the olefin of group (c) above; and II. a polyamine in a relative proportion of about 0.1 to 0.5 mole of polyamine per atom of phosphorus in said adduct, said polyamine containing 2 to 12 nitrogen atoms wherein pairs of nitrogen atoms are joined by alkylene groups of 2 to 4 carbon atoms, and being selected from the group consisting of polyamines defined by the formulae:

$$NH_2(CH_2)_n - [NH(CH_2)_n]_m - NH_2 \quad (a)$$

(b)

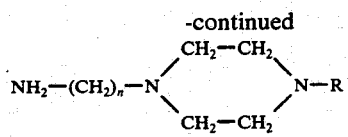

wherein: $n$ is 2 to 4 and R is selected from the group consisting of hydrogen and aminoalkyl radicals of 2 to 3 carbon atoms; and

(c)

wherein $R_1$ is a $C_2$ to $C_4$ alkylene radical, and $R_2$ and $R_3$ are $C_1$ to $C_5$ alkyl radicals, wherein a molar proportion of said adduct has been reacted, at a temperature in the range of 0° to 100° C., with said polyamine.

* * * * *